United States Patent
Nishizawa et al.

(10) Patent No.: US 6,852,862 B2
(45) Date of Patent: Feb. 8, 2005

(54) PROCESS FOR PRODUCING QUINOLINE-3-CARBOXYLIC ACID COMPOUND

(75) Inventors: Susumu Nishizawa, Osaka (JP); Sadanobu Yoshikawa, Kashiba (JP)

(73) Assignees: Sumika Fine Chemicals Co., Ltd., Osaka (JP); Nissan Chemical Industries, Ltd., Tokyo (JP)

(*) Notice: Subject to any disclaimer, the term of this patent is extended or adjusted under 35 U.S.C. 154(b) by 0 days.

(21) Appl. No.: 10/468,350

(22) PCT Filed: Feb. 25, 2002

(86) PCT No.: PCT/JP02/01645
§ 371 (c)(1),
(2), (4) Date: Sep. 24, 2003

(87) PCT Pub. No.: WO02/070488
PCT Pub. Date: Sep. 12, 2002

(65) Prior Publication Data
US 2004/0073034 A1 Apr. 15, 2004

(30) Foreign Application Priority Data
Mar. 2, 2001 (JP) ........................................ 2001-058243

(51) Int. Cl.$^7$ ........................ C07D 215/14; A61K 31/47
(52) U.S. Cl. ........................ 546/170; 546/170; 514/311
(58) Field of Search ............................ 546/170; 514/311

(56) References Cited

U.S. PATENT DOCUMENTS 5,223,513 A * 6/1993 Meguro et al. ............. 514/312

* cited by examiner

Primary Examiner—Joseph K. McKane
Assistant Examiner—Janet L Coppins

(74) Attorney, Agent, or Firm—Oliff & Berridge, PLC

(57) ABSTRACT

A process for producing quinoline-3-carboxylic acid represented by formula

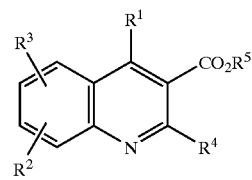

(3)

wherein $R^1$, $R^2$, $R^3$, $R^4$ and $R^5$ have the same meanings as defined below, characterized by reacting 2-aminophenyl ketone represented by formula (1)

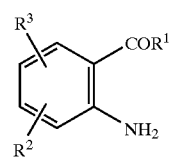

(1)

wherein $R^1$ is an aryl group, a $C_{1-12}$ alkyl group which may be branched, etc., and $R^2$ and $R^3$ are each a hydrogen atom, a halogen atom, a $C_{1-12}$ alkyl group which may be branched, etc., with a keto ester represented by formula (2)

$$R^4COCH_2CO_2R^5 \qquad (2)$$

wherein $R^4$ is a $C_{1-12}$ alkyl group which may be branched, a $C_{3-6}$ cycloalkyl group, etc., and $R^5$ is a $C_{1-6}$ alkyl group which may be branched,
in the presence of an acid catalyst in an alcohol solvent while distilling off the alcohol.

11 Claims, No Drawings

PROCESS FOR PRODUCING QUINOLINE-3-CARBOXYLIC ACID COMPOUND

TECHNICAL FIELD

The present invention relates to a process for producing quinoline-3-carboxylic acid compound that is an intermediate useful for cholesterol lowering agents (HMG-CoA reductase inhibitors), for example pharmaceuticals disclosed in Japanese Patent Laid-open No. Hei 1-279866, EP 0 304 063 A or U.S. Pat. No. 5,011,930.

BACKGROUND ART

Conventionally, various processes for producing quinoline-3-carboxylic acid compounds have bee proposed. These processes include, for example i) a process comprising condensing 2-aminophenyl ketones with keto esters in the presence of a sulfuric acid catalyst in an acetic acid solvent to produce quinoline-3-carboxylic acid compounds, ii) a process comprising dehydrating and condensing 2-aminophenyl ketones with keto esters in the presence of an acid catalyst in a hydrocarbon solvent to produce quinoline-3-carboxylic acid compounds, and the like. The process i) has problems that yields are low as the keto esters are unstable to acids and that the process needs a large amount of acetic acid. Although the process ii) forms a skeleton of quinoline by carrying out dehydration and condensation in a hydrocarbon solvent such as toluene or the like, the process requires a rapid progress of the reaction as keto esters are unstable similarly to the process i), and therefore the process requires a dehydration and reflux under a reduced pressure or use of an excess of keto esters. In addition, the 2-aminophenyl ketones and resulting quinolines have an alkalinity, thereby they make a salt together with an acid as a catalyst to deposit crystal or oil in the reaction solution. Thus, the process has problems that it is delayed or stopped.

Therefore, an object of the present invention is to provide to a process for producing quinoline-3-carboxylic acid compound that is an intermediate useful for pharmaceuticals, briefly in an industrial scale, and in a high yield and purity.

DISCLOSURE OF INVENTION

The present inventors have eagerly studied in search for a process for producing quinoline-3-carboxylic acid compound that is an intermediate useful for pharmaceuticals, briefly in an industrial scale, and in a high yield and purity, and consequently found a process for producing quinoline-3-carboxylic acid compound that is an intermediate useful for pharmaceuticals, briefly in an industrial scale, and in a high yield and purity, by reacting 2-aminophenyl ketone and an acid catalyst, or instead of them, a salt of 2-aminophenyl ketone with an acid catalyst, with a keto ester, unexpectedly in an alcohol solvent while distilling off the alcohol, and the present inventors completed the present invention.

That is, the present invention relates to a process for producing quinoline-3-carboxylic acid represented by formula (3)

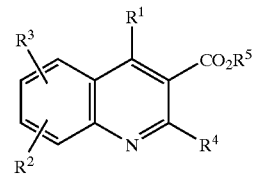

(3)

wherein $R^1$, $R^2$, $R^3$, $R^4$ and $R^5$ have the same meanings as defined below, characterized by reacting 2-aminophenyl ketone represented by formula (1)

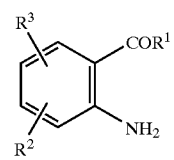

(1)

wherein $R^1$ is an aryl group, a $C_{1-12}$ alkyl group which may be branched, a $C_{2-12}$ alkenyl group which may be branched, a $C_{2-12}$ alkynyl group which may be branched or a $C_{3-6}$ cycloalkyl group, and the aryl, alkyl, alkenyl, alkynyl and cycloalkyl groups may be substituted; and $R^2$ and $R^3$ are each a hydrogen atom, a halogen atom, a $C_{1-12}$ alkyl group which may be branched, a $C_{3-6}$ cycloalkyl group, a $C_{1-12}$ alkyloxy group which may be branched, or an aryl group, and the alkyl, cycloalkyl, alkyloxy and aryl groups may be substituted, with a keto ester represented by formula (2)

$$R^4COCH_2CO_2R^5 \qquad (2)$$

wherein $R^4$ is a $C_{1-12}$ alkyl group which may be branched, a $C_{3-6}$ cycloalkyl group, or an aryl group, and the alkyl, cycloalkyl and aryl groups may be substituted, and $R^5$ is a $C_{1-6}$ alkyl group which may be branched, in the presence of an acid catalyst in an alcohol solvent while distilling off the alcohol.

Preferable embodiments of the present invention are as follows:

(1) The process in which the alcohol solvent is at least one selected from the group consisting of ethanol, 1-propanol, 2-propanol and 2-butanol;

(2) The process in which a salt formed by reaction of an acid catalyst with 2-aminophenyl ketone is used;

(3) The process in which the acid catalyst is methanesulfonic acid; and (4) The process in which $R^1$ is 4-fluorophenyl, $R^2$ and $R^3$ are each a hydrogen atom, $R^4$ is isopropyl or cyclopropyl, and $R^5$ is a $C_{1-4}$ alkyl group.

$C_{1-12}$ alkyl group which may be branched, represented by $R^1$, $R^2$, $R^3$ and $R^4$ in the general formulae includes, for example methyl, ethyl, propyl, isopropyl, butyl, isobutyl, sec-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2- methylpropyl, heptyl, octyl, nonyl, decyl, undecyl and dodecyl. These alkyl groups may be substituted.

$C_{3-6}$ cycloalkyl group represented by $R^1$, $R^2$, $R^3$ and $R^4$ in the general formulae includes, for example cyclopropyl, cyclobutyl, cyclopentyl and cyclohexyl. These cycloalkyl groups may be substituted.

The aryl group represented by $R^1$, $R^2$, $R^3$ and $R^4$ in the general formulae includes, for example phenyl, 1-indenyl, 2-indenyl, 3-indenyl, 4-indenyl, 5-indenyl, 6-indenyl, 7-indenyl, 1-naphthyl, 2-naphthyl, 1-tetrahydronaphthyl, 2-tetrahydronaphthyl, 5-tetrahydronaphthyl and 6-tetrahydronaphthyl, and preferably phenyl, 1-naphthyl, 2-naphthyl, 1-tetrahydronaphthyl and 2-tetrahydronaphthyl. These aryl groups may be substituted.

$C_{2-12}$ alkenyl group which may be branched, represented by $R^1$ in the general formulae includes, for example ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-isopropylethenyl, 1,2-dimethyl-1-propenyl, 1,2-dimethyl-2-propenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-butylethenyl, 2-methyl-1-pentenyl, 2-methyl-2-pentenyl, 2-methyl-3-pentenyl, 2-methyl-4-pentenyl, 2-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-sec-butylethenyl, 1,3-dimethyl-1-butenyl, 1,3-dimethyl-2-butenyl, 1,3-dimethyl-3-butenyl, 1-isobutylethenyl, 2,2-dimethyl-3-butenyl, 2,3-dimethyl-1-butenyl, 2,3-dimethyl-2-butenyl, 2,3-dimethyl-3-butenyl, 2-isopropyl-2-propenyl, 3,3-dimethyl-1-butenyl, 1-ethyl-1-butenyl, 1-ethyl-2-butenyl, 1-ethyl-3-butenyl, 1-propyl-1-propenyl, 1-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-isopropyl-1-propenyl and 1-isopropyl-2-propenyl. These alkenyl groups may be substituted.

$C_{2-12}$ alkynyl group which may be branched, represented by $R^1$ in the general formulae includes, for example ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 2-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 1-propyl-2-propynyl, 2-ethyl-3-butynyl, 1-methyl-1-ethyl-2-propynyl and 1-isopropyl-2-propynyl. These alkynyl groups may be substituted.

$C_{1-12}$ alkyloxy group which may be branched, represented by $R^2$ and $R^3$ in the general formulae includes, for example methoxy, ethoxy, propoxy, isopropoxy, butoxy, isobutoxy, sec-butoxy, t-butoxy, pentyloxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexyloxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropxy. These alkyloxy groups may be substituted.

Halogen atoms represented by $R^2$ and $R^3$ in the general formulae include a fluorine atom, a chlorine atom and a bromine atom, or the like.

The substituents on $R^1$, $R^2$, $R^3$ and $R^4$ groups can be any substituents that do not inhibit the reaction of an aldehyde group, and include, for example a $C_{1-12}$ alkyl group, a $C_{2-12}$ alkenyl group, a $C_{2-12}$ alkynyl group, a $C_{3-6}$ cycloalkyl group, a $C_{1-6}$ alkyloxy group, a halogen atom, an aryl group, such as phenyl or naphthyl, a heterocyclic group, such as pyridyl, pyrimidyl or quinolyl, an aralkyl group, such as benzyl or phenylethyl, an ester group, such as ethoxycarbonyl, a carbonate group, such as ethoxycarbonyloxy, a nitro group, a cyano group, an amide group, an ureido group and a sulfonylamide group.

$C_{1-6}$ alkyl group which may be branched, represented by $R^5$ in the general formulae includes, for example methyl, ethyl, propyl, isopropyl, butyl, isobutyl, sec-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Preferable examples of $R^1$ are phenyl, phenyl substituted with halogen and phenyl substituted with alkyl. More preferable examples are 4-fluorophenyl and 4-methylphenyl.

Preferable examples of $R^2$ and $R^3$ are a hydrogen atom, a halogen atom and a $C_{1-6}$ alkyl group which may be branched. A more preferable example is a hydrogen atom.

Preferable examples of $R^4$ are a $C_{1-6}$ alkyl group which may be branched, and a $C_{3-6}$ cycloalkyl. More preferable examples are isopropyl and cyclopropyl.

Preferable examples of $R^5$ is $C_{1-4}$ alkyl groups which may be branched. More preferable examples are methyl and ethyl.

The alcohol solvent includes ethanol, 1-propanol, 2-propanol and 2-butanol, and is preferably 2-propanol.

These alcohol solvents may be used in a mixture with other solvent, for example esters, such as ethyl acetate, hydrocarbons, such as heptane or toluene, halogenated hydrocarbon, such as dichlorobenzene, ethers, such as tetrahydrofuran. These other solvents can be used in an amount which does not inhibit the reaction. For example, a solvent mixture comprises about 5% of dichlorobenzene based on 2-propanol.

The amount of alcohol solvent to be used is not specifically limited, and generally 200 to 1000 parts by mass, preferably 400 to 800 parts by mass based on 100 parts by mass of 2-aminophenylketone used.

The reaction temperature depends on raw materials, an acid catalyst or a solvent and is not necessarily determined. It ranges usually from 65° C. to 105° C., preferably from 75° C. to 90° C. If it is less than 65° C., reaction rate becomes low. On the other hand, if it is more than 105° C., keto esters become unstable and therefore an excess amount of them is required or yield lowers.

The amount of alcohol solvent distilled off is 450 to 550 parts by mass, preferably 480 to 520 parts by mass based on 100 parts by mass of 2-aminophenylketone used. The distillation off of the alcohol solvent can be carried out under atmospheric pressure or a reduced pressure. When it is carried out under a reduced pressure, the pressure is 70 to 80 kPa, for example.

The acid catalyst includes, for example methanesulfonic acid, p-toluenesulfonic acid, trifluoroacetic acid and trifluoromethanesulfonic acid, and is preferably methanesulfonic acid. A salt formed previously by reaction of an acid catalyst with 2-aminophenyl ketone may be used. In this case, an acid catalyst need not be further added.

An amount of the acid catalyst used is 0.5 to 2.0 times molar quantity, preferably 0.8 to 1.5 times molar quantity based on 1 mole of 2-aminophenyl ketone.

Although reaction time is not necessarily determined, it is usually 1 to 24 hours.

EXAMPLES

The present invention is described on the basis of the following examples which are simply exemplified and to which the present invention is not limited.

Reference Example 1

99.26 g of anthranilic acid was added to 830 g of water, the resulting mixture was heated at 75° C. and 165.3 g of p-toluenesulfonyl chloride was added thereto over 30 minutes with stirring. 495 g of 28% aqueous solution of sodium hydroxide was added dropwise and the mixture was stirred at 80° C. for one hour. The reaction mixture was added dropwise to a mixed solution of 360 g of 35% hydrochloric acid and 270 g of water at 70 to 80° C. and stirred for one hour. After cooling to 30° C., the mixture was filtered, the resulting crystals were washed with water, and the wet crystals were heated and solved in 750 g of 1-propanol to obtain a solution. After cooling to a room temperature, the solution was filtered, the resulting crystals were washed with 1-propanol, and dried under a reduced pressure to obtain 175 g of N-tosyl anthranilic acid.

Yield: 83%

NMR (DMSO, $d_6$, δ, ppm): 2.339 (S, 3H, methyl), 3.32 (br, 1H, COOH), 7.1–7.13 (m, 1H, aromatic nucleus), 7.344 (t, 2H, aromatic nucleus), 7.526 (t, 2H, aromatic nucleus), 7.696 (d, 2H, aromatic nucleus), 7.898 (d, 1H, aromatic nucleus), 11.1 (brS, 1H, NH)

Reference Example 2

50 g of N-tosyl anthranilic acid and 130 mg of dimethylformamide were added to 275 g of o-dichlorobenzene, the resulting mixture was heated at 80° C. Then, 24.5 g of thionyl chloride was added dropwise thereto and the mixture was kept at the same temperature. The reaction mixture was concentrated at an internal temperature of 70 to 75° C. under a reduced pressure of about 2 kPa. After distilling off about 10% of o-dichlorobenzene, 11.6 g of o-dichlorobenzene and 65.97 g of fluorobenzene were added. A solution comprising 137 g of o-dichlorobenzene and 73.23 g of anhydrous aluminum chloride was prepared separately, and to this solution the above-mentioned reaction mixture was added dropwise at a temperature of 20 to 25° C. The mixture was heated and kept at 90° C. for 3 hours. The reaction mixture was added dropwise to 300 g of water, and separated into phases at about 70° C. Then, the organic phase was washed with 5% brine solution and then water. Under a reduced pressure, o-dichlorobenzene was distilled off, 250 g of ethyl acetate was added and solved, and then crystals were separated out by adding 16.5 g of methanesulfonic acid dropwise. The organic phase was filtered and dried to obtain 46.1 g of 2-amino-4'-fluorobenzophenone methanesulfonate.

Yield: 86%

NMR (DMSO, $d_6$, δ, ppm): 2.522 (S, 3H, methyl), 6.703 (m, 1H, aromatic nucleus), 7.00 (d, 1H, aromatic nucleus), 7.3–8.3 (m, 11H, aromatic nucleus+$NH_2$+$SO_3H$)

Reference Example 3

30 g of 2-amino-4'-fluorobenzophenone methanesulfonate was added to 150 g of o-dichlorobenzene, the resulting mixture was heated at 80° C. Then, the reaction solution was made alkaline with 25% aqueous solution of sodium hydroxide. The reaction solution was separated into phases at the same temperature and washed with 5% brine solution. The organic phase was dried over anhydrous magnesium sulfate, and filtered at 80° C. The filtrate was gradually cooled, stirred at 0 to 5° C. for 4 hours, filtered and washed with a small amount of toluene. After drying, 19 g of 2-amino-4'-fluorobenzophenone was obtained.

Yield: 92%

Melting point: 127–130° C.

NMR (DMSO, $d_6$, δ, ppm): 6.02 (S, 2H, $NH_2$), 3.32 (br, 1H, COOH), 6.616 (m, 1H, aromatic nucleus), 6.74 (q, 1H, aromatic nucleus), 7.136 (m, 2H, aromatic nucleus), 7.296 (m, 1H, aromatic nucleus), 7.41 (d, 1H, aromatic nucleus), 7.675 (m, 2H, aromatic nucleus)

Example 1

12 g of methyl 3-cyclopropyl-3-oxopropionate and 25 g of 2-amino-4'-fluorobenzophenone methanesulfonate were added to 146 g of 2-propanol, and 2-propanol was distilled off at 79 to 83° C. After distilling off 119 g of 2-propanol over 6 hours, 1.14 g of methyl 3-cyclopropyl-3-oxopropionate was added and the mixture was heated at 79 to 81° C. for 4 hours. An analysis of the mixture with high performance liquid chromatography (HPLC) showed that the residual amount of 2-amino-4'-fluorobenzophenone as a raw material was 0.9%. 146 g of toluene was added into the reaction solution, and the reaction solution was washed with 80 g of 4% aqueous solution of sodium hydroxide and then 35 g of 2% aqueous solution of sodium hydroxide. The reaction solution was further washed with 25 g of 5% brine solution, and then dried over 5 g of anhydrous magnesium sulfate. Toluene was removed under a reduced pressure, and crystallization was carried out in 180 g of cyclohexane to obtain 22.9 g of methyl 2-cyclopropyl-4-(4'-fluorophenyl) quinoline-3-carboxylate.

Yield: 89.0%

HPLC purity: 99.7%

NMR ($CDCl_3$, δ, ppm): 1.04–1.08 (m, 2H, cyclopropane ring), 1.34–1.38 (m, 2H, cyclopropane ring), 2.16–2.2 (m, 1H, cyclopropane ring), 3.63 (S, 3H, methyl), 7.17–7.21 (m, 2H, aromatic nucleus), 7.33–7.39 (m, 3H, aromatic nucleus), 7.477–7.50 (m, 1H, aromatic nucleus), 7.645–7.685 (t, 1H, aromatic nucleus), 7.973–7.993 (d, 1H, aromatic nucleus)

Example 2

92 g of methyl 3-cyclopropyl-3-oxopropionate and 130.3 g of 2-amino-4'-fluorobenzophenone and 58.2 g of methanesulfonic acid were added to 1100 g of 2-propanol, and 2-propanol was distilled off at 80 to 87° C. After distilling off 984 g of 2-propanol over 5 hours, 6.85 g of methyl 3-cyclopropyl-3-oxopropionate was added and the mixture was heated at 80° C. for 3 hours. An analysis of the mixture with HPLC showed disappearance of 2-amino-4'-fluorobenzophenone as a raw material. 1100 g of toluene was added into the reaction solution, and the reaction solution was washed with 602 g of 4% aqueous solution of sodium hydroxide and then 262 g of 2% aqueous solution of sodium hydroxide. The reaction solution was further washed with 206 g of 5% brine solution, and then dried over 21 g of anhydrous magnesium sulfate. An analysis of the toluene solution with HPLC showed that 186.5 g of methyl 2-cyclopropyl-4-(4'-fluorophenyl)quinoline-3-carboxylate was produced (converted yield: 96%).

Example 3

694.1 kg of methyl 3-cyclopropyl-3-oxopropionate and 1447.8 kg of 2-amino-4'-fluorobenzophenone methanesulfonate were added to 8455 kg of 2-propanol, and 2-propanol was distilled off at 79 to 87° C. After distilling off 7553 kg of 2-propanol, 66.1 kg of methyl 3-cyclopropyl-3-oxopropionate was added and the mixture was heated at 79 to 81° C. for 4 hours. An analysis of the mixture with HPLC showed that the residual amount of 2-amino-4'-fluorobenzophenone as a raw material was 0.5%. 8455 kg of toluene was added into the reaction solution, and the reaction solution was washed with 4620 kg of 4% aqueous solution of sodium hydroxide, then 2010 kg of 2% aqueous solution of sodium hydroxide, and finally 1585 kg of 5% brine solution. The reaction solution was dried over 158 kg of anhydrous magnesium sulfate to obtain 10220 kg of a toluene solution containing 1350 kg of methyl 2-cyclopropyl-4-(4'-fluorophenyl)quinoline-3-carboxylate (converted yield: 90.4%). A part of the solution was concentrated, and the concentrated residue was recrystallized from toluene having the same mass as that of the residue and heptane having five times mass of the residue to obtain methyl 2-cyclopropyl-4-(4'-fluorophenyl)quinoline-3-carboxylate of HPLC purity 99.7%. The substance has the same properties as the substance of Example 1.

Comparative Example 1

47.9 g of methyl 3-cyclopropyl-3-oxopropionate and 100 g of 2-amino-4'-fluorobenzophenone methanesulfonate were added to 584 g of toluene, and the mixture was dehydrated and refluxed at an internal temperature of 79 to 81° C. under a reduced pressure of 40 kPa. The reaction mixture was analyzed with HPLC during the reaction, and methyl 3-cyclopropyl-3-oxopropionate was added thereto by dividing it into several parts until the residual amount of 2-amino-4'-fluorobenzophenone was less than 2%. An additional amount of methyl 3-cyclopropyl-3-oxopropionate was 13.8 g. After 40 hours of reaction time, the residual amount of 2-amino-4'-fluorobenzophenone was 1.7%. The reaction solution was washed with 320 g of 4% aqueous solution of sodium hydroxide and then 140 g of 2% aqueous solution of sodium hydroxide. The reaction solution was further washed with 100 g of 5% brine solution, and then dried over 10 g of anhydrous magnesium sulfate. Toluene was removed under a reduced pressure, and crystallization was carried out in 740 g of cyclohexane to obtain 88.4 g of methyl 2-cyclopropyl-4-(4'-fluorophenyl)quinoline-3-carboxylate.

Yield: 85.6%

HPLC purity: 98.9%

INDUSTRIAL APPLICABILITY

As mentioned above, the process of the present invention exerts an effect that quinoline-3-carboxylic acid compound that is an intermediate useful for pharmaceuticals can be produced briefly in an industrial scale, and in a high yield and purity.

What is claimed is:

1. A process for producing quinoline-3-carboxylic acid represented by formula (3)

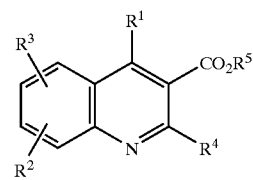

(3)

wherein $R^1$, $R^2$, $R^3$, $R^4$ and $R^5$ have the same meanings as defined below, characterized by reacting 2-aminophenyl ketone represented by formula (1)

(1)

wherein $R^1$ is an aryl group, a $C_{1-12}$ alkyl group which may be branched, a $C_{2-12}$ alkenyl group which may be branched, a $C_{2-12}$ alkynyl group which may be branched or a $C_{3-6}$ cycloalkyl group, and the aryl, alkyl, alkenyl, alkynyl and cycloalkyl groups may be substituted; and $R^2$ and $R^3$ are each a hydrogen atom, a halogen atom, a $C_{1-12}$ alkyl group which may be branched, a $C_{3-6}$ cycloalkyl group, a $C_{1-12}$ alkyloxy group which may be branched, or an aryl group, and the alkyl, cycloalkyl, alkyloxy and aryl groups may be substituted, with a keto ester represented by formula (2)

$R^4COCH_2CO_2R^5$ (2)

wherein $R^4$ is a $C_{1-12}$ alkyl group which may be branched, a $C_{3-6}$ cycloalkyl group, or an aryl group, and the alkyl, cycloalkyl and aryl groups may be substituted, and $R^5$ is a $C_{1-6}$ alkyl group which may be branched, in the presence of an acid catalyst in an alcohol solvent and distilling off the alcohol during the reaction of the 2-aminophenyl ketone with the keto ester.

2. The process for producing quinoline-3-carboxylic acid according to claim 1, wherein the alcohol solvent is at least one selected from the group consisting of ethanol, 1-propanol, 2-propanol and 2-butanol.

3. A process for producing quinoline-3-carboxylic acid represented by formula (3)

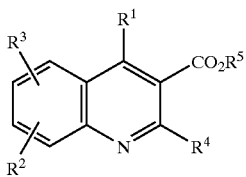

(3)

wherein $R^1$, $R^2$, $R^3$, $R^4$, and $R^5$ have the same meanings as defined below, characterized by reacting a salt formed by reaction of an acid catalyst with 2-aminophenyl ketone represented by formula (1)

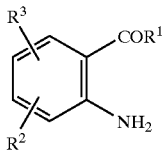

(1)

wherein $R^1$ is an aryl group, a $C_{1-12}$ alkyl group which may be branched, a $C_{2-12}$ alkenyl group which may be branched, a $C_{2-12}$ alkynyl group which may be branched or a $C_{3-6}$ cycloalkyl group, and the aryl, alkyl, alkenyl, alkynyl and cycloalkyl groups may be substituted; and $R^2$ and $R^3$ are each a hydrogen atom, a halogen atom, a $C_{1-12}$ alkyl group which may be branched, a $C_{3-6}$ cycloalkyl group, a $C_{1-12}$ alkyloxy group which may be branched, or an aryl group, and the alkyl, cycloalkyl, alkyloxy and aryl groups may be substituted, with a keto ester represented by formula (2)

$$R^4COCH_2CO_2R^5 \qquad (2)$$

wherein $R^4$ is a $C_{1-12}$ alkyl group which may be branched, a $C_{3-6}$ cycloalkyl group, or and aryl group, and the alkyl, cycloalkyl and aryl groups may be substituted, and $R^5$ is a $C_{1-6}$ alkyl group which may be branched, in an alcohol solvent and distilling off the alcohol during the reaction of the salt with the keto ester.

4. The process for producing quinoline-3-carboxylic acid according to claim 1, wherein the acid catalyst is methanesulfonic acid.

5. The process for producing quinoline-3-carboxylic acid according to claim 1, wherein $R^1$ is 4-fluorophenyl, $R^2$ and $R^3$ are each a hydrogen atom, $R^4$ is isopropyl or cyclopropyl, and $R^5$ is a $C_{1-4}$ alkyl group.

6. The process for producing quinoline-3-carboxylic acid according to claim 2, wherein the acid catalyst is methanesulfonic acid.

7. The process for producing quinoline-3-carboxylic acid according to claim 3, wherein the acid catalyst is methanesulfonic acid.

8. The process for producing quinoline-3-carboxylic acid according to claim 2, wherein $R^1$ is 4-fluorophenyl, $R^2$ and $R^3$ are each a hydrogen atom, $R^4$ is isopropyl or cyclopropyl, and $R^5$ is a $C_{1-4}$ alkyl group.

9. The process for producing quinoline-3-carboxylic acid according to claim 3, wherein $R^1$ is 4-fluorophenyl, $R^2$ and $R^3$ are each a hydrogen atom, $R^4$ is isopropyl or cyclopropyl, and $R^5$ is a $C_{1-4}$ alkyl group.

10. The process for producing quinoline-3-carboxylic acid according to claim 4, wherein $R^1$ is 4-fluorophenyl, $R^2$ and $R^3$ are each a hydrogen atom, $R^4$ is isopropyl or cyclopropyl, and $R^5$ is a $C_{1-4}$ alkyl group.

11. The process for producing quinoline-3-carboxylic acid according to claim 3, wherein the alcohol solvent is at least one solvent selected from the group consisting of ethanol, 1-propanol, 2-propanol and 2-butanol.

\* \* \* \* \*